United States Patent [19]
Gottesman

[11] Patent Number: 4,834,068
[45] Date of Patent: May 30, 1989

[54] BARRIER SHIELD METHOD AND APPARATUS FOR OPTICAL-MEDICAL DEVICES

[76] Inventor: James E. Gottesman, 2025 - 80th Ave., SE., Mercer Island, Wash. 98040

[21] Appl. No.: 169,742

[22] Filed: Mar. 18, 1988

[51] Int. Cl.$^4$ ............................................. A61B 1/00
[52] U.S. Cl. ........................................ 128/4; 128/846; 128/857
[58] Field of Search ............... 128/132 R, 132 D, 3, 128/4, 5, 6, 7, 849, 851, 856, 857, 858, 897, 898, 846; 604/97

[56] References Cited

U.S. PATENT DOCUMENTS

| | | | |
|---|---|---|---|
| 3,766,920 | 10/1973 | Greene | 604/97 |
| 4,593,681 | 6/1986 | Soni | 128/4 |
| 4,616,641 | 10/1986 | Teeple | 128/132 R |

Primary Examiner—William H. Grieb
Attorney, Agent, or Firm—Seed and Berry

[57] ABSTRACT

A barrier shield for optical-medical devices is disclosed which has an inner aperture defined by an elastic material so as to form a seal adjacent to an optical portion of the device. The shield extends radially from the elastic material and may be supported by a frame. The elastic material permits movement of the shield about its position with respect to the optical-medical device so that operation of working ports is not impaired. The shield is manufactured from inexpensive materials so as to encourage disposal of the shield after use. The shield prevents infection of a physician by preventing backspray of bodily fluids through a optical-medical device working port from reaching the physician. The shield also helps prevent reverse contamination of working devices passed into the patient during endoscopy.

1 Claim, 2 Drawing Sheets

BARRIER SHIELD METHOD AND APPARATUS FOR OPTICAL-MEDICAL DEVICES

TECHNICAL FIELD

The invention relates to barrier techniques for the prevention of infection by bodily fluids. More specifically, the invention relates to devices and techniques for preventing infection of physicians and their staff during endoscopic procedures.

BACKGROUND ART

Modern medical techniques encompass the removal of kidney stones, the performance of biopsies and other operations by passing an endoscope (a telescope-like device, such as a cystoscope, ureteroscope, laparoscope, bronchoscope, colonoscope, arthroscope, etc.) through various orifices in the body. Such procedures often obviate the necessity for open surgery. In a typical endoscopic procedure, such as removal of a stone from a ureter, the endoscopist passes a variety of devices through the urethra, into the bladder and into the ureter in which a stone may be lodged. The stone is then removed in the reverse order.

The above-identified optical-medical devices generically include an optical pathway with one or more working ports adjacent to an eyepiece of the optical pathway. The working ports include valves which are opened to allow the endoscopist to pass tubes, biopsy forceps, grasping forceps, laser fibers, catheters, etc., through the ports and into the appropriate passageway or organ in the body. The working ports are partially sealed by rubber diaphragms while the working devices are passing through the ports. During these procedures, the bladder, for example, is irrigated with water (that is, the bladder is pressurized with water through the endoscope) to prevent the bladder from occluding the end of the optical pathway and to prevent orifices such as the ureteral orifices from being obscured. Thus, the working ports are continually leaking fluid (water mixed with various bodily fluids). When a working device is used through a working port, a stream of fluid may exit the working port adjacent to the eyepiece so as to splash the endoscopist. This may occur at the time the working device is removed. The fluid may continuously exit around the working device because the seal between the device and the working port is not fluid tight. While the physician is typically wearing a mask, gloves and perhaps eye protection, a common occurrence is for fluid to enter the eye of the physician.

In a typical situation, a patient with a stone lodged in the ureter may undergo endoscopic treatment to remove the stone. A cystoscope having one or more working ports is first passed through the urethra so that the ureteral orifice can be located inside the bladder. Water is introduced into the bladder under pressure through the cystoscope to distend the bladder, as described above. The ureteral orifice of interest is located and a guidewire is passed through one of the open working ports into the ureter. The guidewire is narrower than the opening of the port and a backspray of irrigating fluid mixed with bodily fluid occurs. The bodily fluids often include blood because the ureter is already inflamed or cut by the stone lodged therein.

The cystoscope is then removed, leaving the guidewire in place, and a catheter with a dilating balloon (similar to an angioplastic balloon) is passed over the guidewire. The balloon cracks the ureter up to the position of the stone to allow the subsequent passage of a ureteroscope over the guidewire. The ureteroscope is passed over the guidewire and into the ureter until the end of the ureteroscope is positioned adjacent to the stone. The ureteroscope's working port is then opened so that a stone grasping basket can be passed there through to the position of the stone. While the working port is opened and while the stone grasping basket is passed through the working port, backflow occurs and the physician is again sprayed with a mixture of water, blood and other bodily fluids. To maintain the ureteral wall dilated so that the basket can grasp the stone, a high-pressure water flow is introduced into the ureteroscope and ureter, resulting in substantial backspray during manipulation of the grasping basket. The stone is then grasped by the grasping basket, and the grasping basket, with the stone and ureteroscope are removed. The cystoscope is then reinserted into the urethra so that a stent can be placed into the ureter to aid in healing thereof.

As is apparent from the above, throughout the procedure, the physician is continuously exposed to backpressure spray from the working port, either while the working ports are open or while a working tool is being inserted or removed through the working port.

As is well known, the occurrence of Acquired Immune Deficiency Syndrome (AIDS) and Hepatitis B (viruses) merits serious concern for health care professionals, especially those in contact with bodily fluids, as these workers are at the highest risk of infection. It has been shown that the virus responsible for AIDS (Human Immunodeficiency Virus, HIV) is contained in the bodily fluids described above and that contamination and spread could occur if mucous membranes, open cuts, conjunctivae or puncture wounds were contacted. The Hepatitis B virus can be transmitted through contaminated blood and is significantly more infectious than HIV. Therefore, a need exists for a method and device which can be used with conventional endoscopic devices to shield the endoscopist from backpressure spray from the working ports.

In addition to the above, reverse contamination from the endoscopist to the patient can occur because the wires and catheters are being passed into and out of the working ports adjacent to the physician's face. Contamination from the physician's mask and face are easily encountered, thereby introducing possible infection into the patient's bladder and ureter. Therefore, a need also exists for a method and device to prevent reverse contamination during endoscopic procedures.

SUMMARY OF THE INVENTION

It is an object of the invention to provide a method and apparatus for shielding endoscopists from backpressure spray of working ports on an optical-medical device.

It is a further object of the invention to achieve the above object without substantially impairing an endoscopist's ability to manipulate working tools through the working ports of an optical-medical device.

It is yet another object of the present invention to achieve the above two objects with a device which can be produced so as to be sterile and which is relatively inexpensive so that the device can be discarded after use.

It is still another object of the present invention to prevent contamination of the devices passed into endoscopes by providing a sterile barrier between the patient and the endoscopist.

The invention achieves these objects, and other objects and advantages which will become apparent from the description which follows, by providing a shield which is positionable between the eyepiece of an optical-medical device and the working ports of such a device.

In the preferred embodiment, the shield includes an elastic member which defines an aperture. The aperture has a relaxed diameter sufficiently small to seal a portion of the optical-medical device between the eyepiece and the working port and a tension diameter sufficiently large to permit passage of the eyepiece therethrough. A shield portion is integral with the elastic member and extends radially therefrom. The shield protects the physician from backpressure spray from the working ports and cooperates with the elastic member to allow the physician to manipulate working tools through the working ports. The shield is preferably manufactured from a clear material which allows the physician to see through the shield. The position of the aperture defined by the elastic member with respect to the perimeter of the shield may be varied to accommodate different optical-medical instruments. For example, for use with some instruments, the aperture may be centrally located with respect to the perimeter of the shield while for other applications the aperture may be located off-center.

BEST MODE FOR CARRYING OUT THE INVENTION

Figure 1:
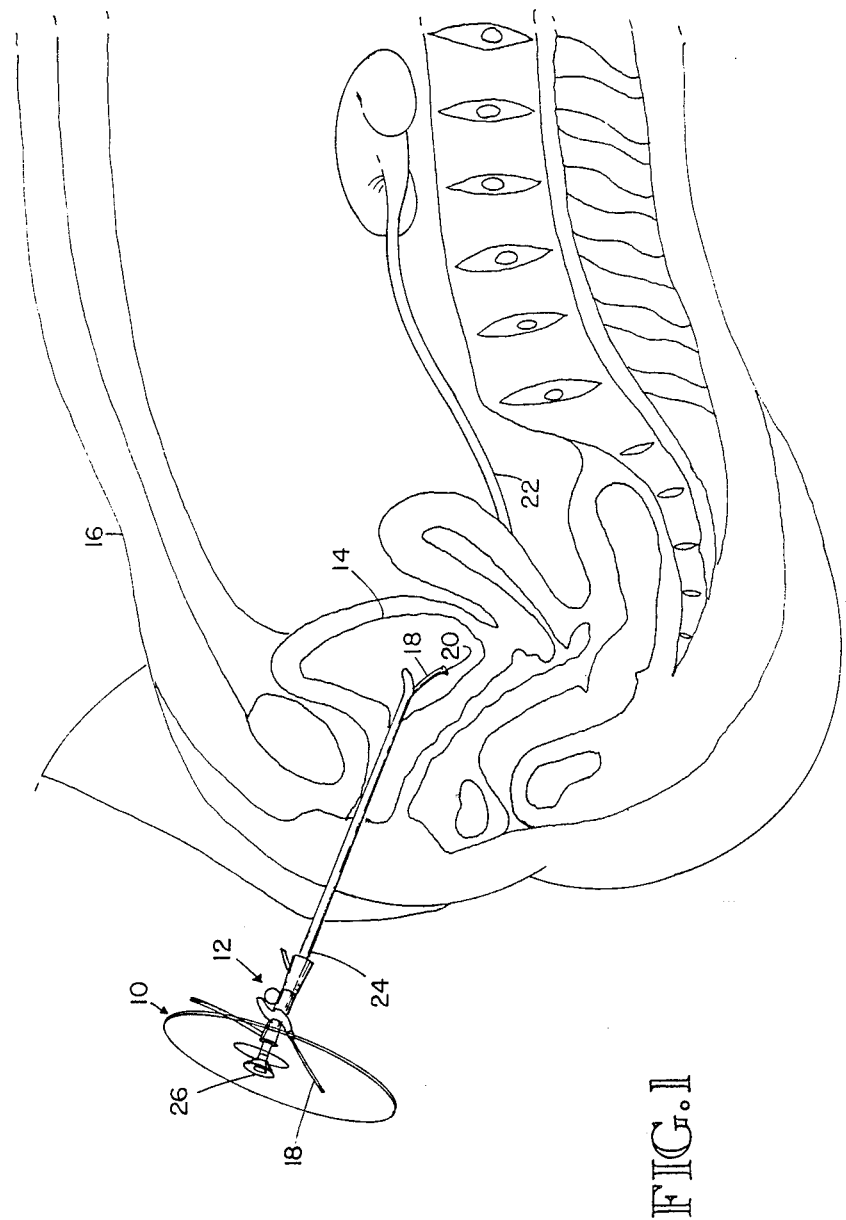
FIG. 1 is a sectional schematic representation of a female undergoing an endoscopic procedure with the shield of the present invention in place.

A barrier shield, in accordance with the present invention, is generally indicated at reference numeral 10 in FIG. 1. The shield is shown in use on a conventional cystoscope generally indicated at reference numeral 12. The cystoscope is shown inserted into the bladder 14 of a patient 16 so that a catheter, guidewire, etc., 18 may be passed through the ureteral orifice 20 and into the ureter 22.

Figure 2:
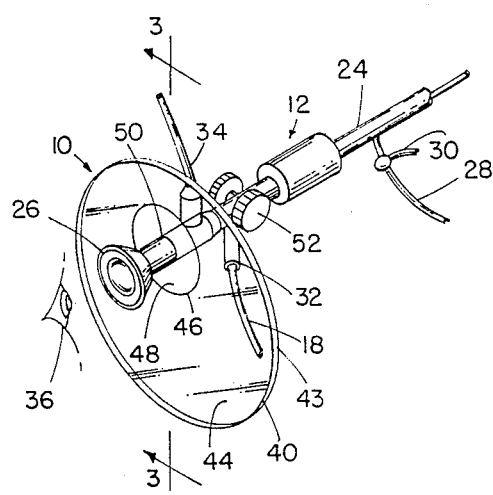
FIG. 2 is a partial isometric view of a cystoscope with the shield in place.
Figure 3:
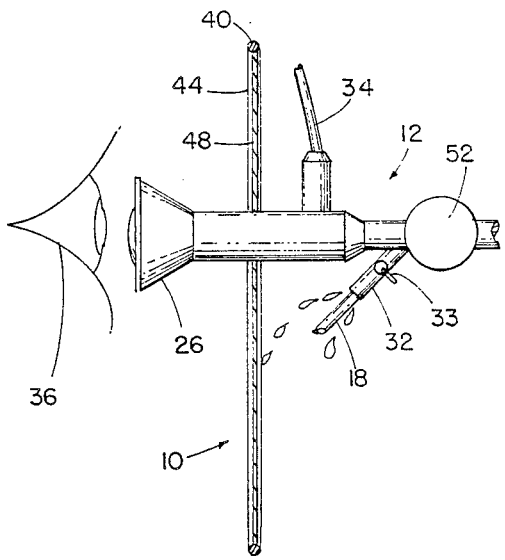
FIG. 3 is a sectional elevational view taken along line 3—3 of FIG. 2.

As best seen in FIGS. 2 and 3, the cystoscope 12 has an elongated projection 24 containing an optical system having an eyepiece 26. The projection also includes an internal irrigation passageway (not shown) connected to a water supply tube 28 by a valve 30. Adjacent to the eyepiece 26 is a working port 32 (only one working port is shown, whereas two working ports may also be provided). The working port communicates with the internal irrigation passageway through a valve 33 and includes a seal which allows the passage of a catheter, guidewire, etc., 18 therethrough. The seal continually leaks while the catheter, guidewire, etc., 18 is inserted therein due to the water pressure in the projection 24. An illumination source 34 for the optical system is also typically provided in such instruments.

The barrier shield 10 prevents backspray through the seal on the working port 32 from impinging upon the eye 36 of the endoscopist. The shield has a circular frame 40 made from wire, plastic or any other suitable material. The frame is connected to the outer circumference 43 of an annular shield material 44 to support the shield material. The shield material is preferably fluid-impermeable and transparent so as to be optically clear and may be, for example, polyethylene. The shield has an inner circumference 46 to which is attached an elastic annulus 48. The elastic annulus defines variable-diameter aperture 50. The elastic annulus is preferably made from a latex material. The aperture 50 preferably has a relaxed diameter sufficiently small to provide a fluid-tight seal between the eyepiece 26 and the working port 32 on the cystoscope 12. The aperture 50 preferably has a tensioned diameter sufficiently large to allow the eyepiece 26 to pass therethrough. The relaxed and tensioned diameters may be, for example, 0.25 inch and 1.25 inch, respectively. The resilient nature of the elastic annulus permits the shield to be moved while in the position shown. Thus, valve 33, deflector 52 and catheter 18 are not impaired by manipulation.

As shown in FIG. 3, the elastic annulus 48 may be positioned off-center with respect to the outer circumference 43 of the shield material 44 for use with cystoscopes of the type shown wherein the working port 32 is positioned below the eyepiece. For cystoscopes with other working port arrangements, the aperture 50 may be appropriately located.

In use, the barrier shield 10 is installed on the cystoscope 12 or other optical-medical device after the device is inserted into the appropriate body orifice. At all times, the endoscopists should be appropriately protected with gloves, a face mask and eye protection whenever a procedure is performed on a high-risk patient. The materials from which the endoscope is made are preferably sterile before use and the barrier shield is discarded after the procedure is completed.

Those of ordinary skill in the art will readily appreciate variations of the invention after reviewing the above description of the preferred embodiment. For example, the material from which the elastic annulus 48 is made and shield material 44 may be identical so long as the barrier shield is sufficiently translucent and optically clear that operation of the working port is not impaired. In addition, while the preferred diameters for the barrier shield are 6 inches, 9 inches and 12 inches, the shield may be provided in shapes which are noncircular and in other sizes. Therefore, the invention is not to be limited by the above description but is to be determined in scope by the claim which follows.

I claim:

1. A method for shielding a physician from backpressure spray of an optical-medical device, wherein the optical-medical device is of the type having an eyepiece and at least one working port for the insertion of a catheter-like device, comprising the steps of:

providing a spray shield having an elastic member defining an aperture, the aperture having a relaxed diameter sufficiently small to substantially seal a portion of the optical-medical device between the eyepiece and the working port and a tensioned diameter sufficiently large to permit passage of the eyepiece therethrough;

enlarging the aperture by tensioning the elastic member;

passing the eyepiece through the enlarged aperture;

positioning the spray shield between the eyepiece and the working port; and sealing the elastic member about the portion of the optical-medical instrument by releasing the tension thereon.

* * * * *